United States Patent
Bays et al.

(10) Patent No.: US 6,451,013 B1
(45) Date of Patent: Sep. 17, 2002

(54) METHODS OF TONSIL REDUCTION USING HIGH INTENSITY FOCUSED ULTRASOUND TO FORM AN ABLATED TISSUE AREA CONTAINING A PLURALITY OF LESIONS

(75) Inventors: F. Barry Bays, Collierville, TN (US); James B. Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 58 days.

(21) Appl. No.: 09/629,842

(22) Filed: Jul. 31, 2000

Related U.S. Application Data (63) Continuation-in-part of application No. 09/487,709, filed on Jan. 19, 2000.

(51) Int. Cl.[7] ............................................... A61B 18/04
(52) U.S. Cl. ............................. 606/27; 606/28; 606/31; 601/2; 601/3; 607/96; 607/134; 128/898
(58) Field of Search ..................... 601/2–4; 604/21–22, 604/114; 606/27–32, 34, 38, 41, 42, 46, 49, 48, 50, 52, 101, 102, 96, 97, 134; 128/898

(56) References Cited

U.S. PATENT DOCUMENTS

| | | | | |
|---|---|---|---|---|
| 5,730,719 A | * | 3/1998 | Edwards | 604/22 |
| 5,895,356 A | * | 4/1999 | Andrus | 601/3 |
| 6,026,816 A | * | 2/2000 | McMillan et al. | 128/898 |
| 6,096,033 A | | 8/2000 | Tu et al. | |
| 6,113,559 A | * | 9/2000 | Klopotek | 601/3 |
| 6,126,657 A | * | 10/2000 | Edwards et al. | 606/45 |
| 6,135,971 A | | 10/2000 | Hutchinson et al. | |
| 6,217,530 B1 | * | 4/2001 | Martin et al. | 601/2 |
| 6,241,753 B1 | * | 6/2001 | Knowlton | 607/99 |
| 6,309,355 B1 | * | 10/2001 | Cain et al. | 601/2 |
| 6,325,769 B1 | * | 12/2001 | Klopotek | 601/2 |

\* cited by examiner

*Primary Examiner*—Linda C. M. Dvorak
*Assistant Examiner*—David M. Ruddy (57) ABSTRACT

A method of tonsil reduction by thermal ablation using high intensity focused ultrasound energy includes the steps of introducing an ultrasound emitting member in a patient's oral cavity, positioning the ultrasound emitting member adjacent an external surface of one of the patient's tonsils, emitting ultrasound energy from the ultrasound emitting member into the tissue of the one tonsil, focusing the ultrasound energy in the one tonsil, ablating the tissue of the one tonsil with the focused ultrasound energy to form an ablated tissue area in the one tonsil containing unablated tissue of the one tonsil and a plurality of lesions at which the tissue of the one tonsil is ablated, and withdrawing the ultrasound emitting member from the oral cavity. The ablated tissue area is surgically removed or is allowed to remain in the patient's body. The lesions may be absorbed by the patient's body and/or remain as altered tissue such that the tonsil is reduced in size to correspondingly increase the size of the patient's airway and/or is stiffened to resist vibration. The lesions can begin a predetermined distance beneath the external surface of the tonsil such that the mucosa is preserved. The lesions end at a predetermined depth so that muscular tissue is not damaged.

23 Claims, 5 Drawing Sheets

METHODS OF TONSIL REDUCTION USING HIGH INTENSITY FOCUSED ULTRASOUND TO FORM AN ABLATED TISSUE AREA CONTAINING A PLURALITY OF LESIONS

CROSS-REFERENCE TO RELATED PATENT APPLICATIONS

This application is a continuation-in-part of prior U.S. patent application Ser. No. 09/487,709 filed Jan. 19, 2000, the disclosure of which is incorporated herein by reference.

This application is related to co-pending U.S. patent applications Ser. No. 09/487,708 filed Jan. 19, 2000 and entitled Methods of Soft Palate Reduction By Thermal Ablation Using High Intensity Focused Ultrasound, Ser. No. 09/487,707 filed Jan. 19, 2000 and entitled Methods of Tongue Reduction By Thermal Ablation Using High Intensity Focused Ultrasound, Ser. No. 09/487,706 filed Jan. 19, 2000 and entitled Methods of Turbinate Or Other Soft Tissue Reduction By Thermal Ablation Using High Intensity Focused Ultrasound, Ser. No. 09/487,705 filed Jan. 19, 2000 and entitled Methods of Skin Rejuvenation By Thermal Stimulation Using High Intensity Focused Ultrasound, Ser. No. 9/488,844 filed Jan. 21, 2000 and entitled Focused Ultrasound Ablation Devices Having Malleable Handle Shafts and Methods of Using the Same, and Ser. No. 09/487,710 filed Jan. 19, 2000 and entitled Focused Ultrasound Ablation Devices Having Selectively Actuatable Ultrasound Emitting Elements and Methods of Using the Same, the disclosures of which are incorporated herein by reference.

This application is also related to co-pending U.S. patent applications entitled Methods of Soft Palate Reduction Using High Intensity Focused Ultrasound To Form An Ablated Tissue Area Containing A Plurality Of Lesions, Methods of Tongue Reduction Using High Intensity Focused Ultrasound To Form An Ablated Tissue Area Containing A Plurality Of Lesions, Methods of Turbinate Or Other Soft Tissue Reduction Using High Intensity Focused Ultrasound To Form An Ablated Tissue Area Containing A Plurality Of Lesions, and Methods of Skin Rejuvenation Using High Intensity Focused Ultrasound To Form An Ablated Tissue Area Containing A Plurality Of Lesions, the disclosures of which are incorporated herein by reference.

BACKGROUND OF THE INVENTION

1. Field of the Invention

The present invention relates generally to the treatment of anatomical tissue of the head and/or neck with high intensity focused ultrasound energy and, more particularly, to tonsil reduction by thermal ablation using high intensity focused ultrasound.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at one or more specific focusing zones within the tissue, thermal effects can be confined to a defined location, region, volume or area, and such location, region, volume or area can be remote from the ultrasound emitting member.

With the use of high intensity focused ultrasound (HIFU), one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue in the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue in a target location, volume, region or area to an ablative temperature creates an ablative lesion in the tissue in the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue in a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various devices and/or methods for treating anatomical tissue with ultrasound have been proposed as represented by U.S. Pat. No. Re. 33,590 to Dory, U.S. Pat. No. 3,990,452 to Murry et al, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,033,456 to Pell et al, U.S. Pat. No. 5,036,855 to Fry et al, U.S. Pat. No. 5,054,470 to Fry et al, U.S. Pat. No. 5,065,761 to Pell, U.S. Pat. No. 5,080,101 to Dory, U.S. Pat. No. 5,080,102 to Dory, U.S. Pat. No. 5,117,832 to Sanghvi et al, U.S. Pat. No. 5,134,988 to Pell et al, U.S. Pat. No. 5,143,074 to Dory, U.S. Pat. No. 5,150,711 to Dory, U.S. Pat. No. 5,150,712 to Dory, U.S. Pat. No. 5,158,070 to Dory, U.S. Pat. No. 5,222,501 to Ideker et al, U.S. Pat. No. 5,267,954 to Nita, U.S. Pat. No. 5,269,291 to Carter, U.S. Pat. No. 5,269,297 to Weng et al, U.S. Pat. No. 5,295,484 to Marcus et al, U.S. Pat. No. 5,304,115 to Pflueger et al, No. 5,312,328 to Nita et al, U.S. Pat. No. 5,318,014 to Carter, U.S. Pat. No. 5,342,292 to Nita et al, U.S. Pat. No. 5,354,258 to Dory, U.S. Pat. No. 5,380,274 to Nita, U.S. Pat. No. 5,391,197 to Burdette et al, U.S. Pat. No. 5,397,301 to Pflueger et al, U.S. Pat. No. 5,409,002 to Pell, U.S. Pat. No. 5,417,672 to Nita et al, U.S. Pat. No. 5,431,621 to Dory, No. 5,431,663 to Carter, U.S. Pat. No. 5,447,509 to Mills et al, U.S. Pat. No. 5,474,530 to Passafaro et al, U.S. Pat. No. 5,492,126 to Hennige et al, U.S. Pat. No. 5,501,655 to Rolt et al, U.S. Pat. No. 5,520,188 to Hennige et al, U.S. Pat. No. 5,542,917 to Nita et al, U.S. Pat. No. 5,620,479 to Diederich, U.S. Pat. No. 5,676,692 to Sanghvi et al, U.S. Pat. No. 5,728,094 to Edwards, U.S. Pat. No. 5,730,719 to Edwards, U.S. Pat. No. 5,733,315 to Burdette et al, U.S. Pat. No. 5,735,280 to Sherman et al, U.S. Pat. No. 5,738,114 to Edwards, U.S. Pat. No. 5,746,224 to Edwards, U.S. Pat. No. 5,762,066 to Law et al, U.S. Pat. No. 5,800,379 to Edwards, U.S. Pat. No. 5,800,429 to Edwards, U.S. Pat. No. 5,800,482 to Pomeranz et al, U.S. Pat. No. 5,807,308 to Edwards, U.S. Pat. No. 5,817,049 to Edwards, U.S. Pat. No. 5,823,197 to Edwards, U.S. Pat. No. 5,827,277 to Edwards, U.S. Pat. No. 5,843,077 to Edwards, U.S. Pat. No. 5,871, 524 to Knowlton, U.S. Pat. No. 5,873,845 to Cline et al, U.S. Pat. No. 5,873,902 to Sanghvi et al, U.S. Pat. No. 5,879,349 to Edwards, U.S. Pat. No. 5,882,302 to Driscoll, Jr. et al, U.S. Pat. No. 5,895,356 to Andrus et al, No. 5,928,169 to Schatzle et al and U.S. Pat. No. 5,938,608 to Bieger et al.

In particular, the use of high intensity focused ultrasound to thermally damage, ablate, coagulate, denature, cauterize, necrotize or destroy a target volume of tissue is exemplified by U.S. Pat. No. Re. 33,590 to Dory, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,036,855 to Fry et al, U.S. Pat. No. 5,054,470 to Fry et al, U.S. Pat. No. 5,080,101 to Dory, U.S. Pat. No. 5,080,102 to Dory, U.S. Pat. No. 5,117,832 to Sanghvi et al, U.S. Pat. No. 5,143,074 to Dory, U.S. Pat. No. 5,150,711 to Dory, U.S. Pat. No. 5,150,712 to Dory, U.S. Pat. No. 5,295,484 to Marcus et al, U.S. Pat. No. 5,354,258 to Dory, U.S. Pat. No. 5,391,197 to Burdette et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,733,315 to Burdette et al, U.S. Pat. No. 5,762,066 to Law et al, U.S. Pat. No. 5,871,524 to Knowlton, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schatzle et al and U.S. Pat. No. 5,938,608 to Bieger et al.

Ablation of anatomical tissue of the head and/or neck in order to treat various airway related disorders or conditions, such as airway obstructions, snoring disorders and sleep apnea syndrome, has been proposed as illustrated by U.S. patents U.S. Pat. No. 5,423,812 to Ellman et al, U.S. Pat. Nos. 5,456,662, 5,514,131, 5,624,439, 5,674,191, 5,707, 349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077 and 5,879,349 to Edwards and WO 97/43970. The latter patents disclose ablation of various structures of the anatomical airway to alleviate or eliminate snoring disorders and/or obstructive sleep apnea syndrome in patients. U.S. Pat. No. 5,423,812 relates to electrosurgical stripping of tissue. U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077, 5,879,349 and WO 97/43970 disclose RF ablation using tissue penetrating electrodes. U.S. Pat. Nos. 5,707,349, 5,728,094, 5,730,719, 5,738,114, 5,746,224, 5,800,379, 5,800,429, 5,807,308, 5,817,049, 5,823,197, 5,827,277, 5,843,077 and 5,879,349 refer to ultrasound as a possible source of ablative energy.

Sleep apnea syndrome is a medical condition characterized by episodes of apnea during sleep causing daytime hypersomnomulence, morning arm aches, intellectual deterioration, cardiac arrhythmias, snoring and/or thrashing during sleep. Snoring disorders are chiefly caused by vibration of tissue or anatomical structures of the airway and/or blockage, obstruction, occlusion or restriction of the airway by tissue or structures thereof.

Treatments for snoring disorders and/or sleep apnea syndrome have included various pharmacological, surgical and physical measures to reduce or eliminate tissue vibrations and/or airway obstructions or restrictions so as to enhance the flow of air through the patient's airway. Pharmacological measures have included the use of medications such as protriptolene, medroxyprogesterone, acetasolemide, theophylline, nicotine and other medications in addition to avoidance of central nervous system depressants such as sedatives or alcohol. Such medications typically have undesirable side effects and are of limited effectiveness. Surgical measures have included uvulopalatal pharyngoplasty, tonsillectomy, surgery to correct severe retrognathia and tracheostomy. Other surgical measures have included removing a portion or portions of anatomical tissue or structures which can obstruct or restrict the patient's airway.

Surgical techniques have been proposed using standard surgical instruments, laser energy and RF energy. Although surgical measures are generally more effective than medications, the risks associated with surgery can be prohibitive and/or are often unacceptable to the patient. In addition, conventional surgery is associated with considerable trauma and pain for the patient as well as the potential for post-operative complications. Laser and RF energy ablation procedures are less invasive than surgery with standard surgical instruments but are difficult to control; and, if too much tissue is ablated, severe consequences may ensue. Multiple ablation treatments are usually required in order to achieve the results desired, and each treatment may cause the patient to experience significant pain for a considerable length of time. Laser and RF energy ablation systems are not able to repeatedly and consistently produce an ablated tissue area of definitive size. Physical measures to treat snoring disorders and/or sleep apnea syndrome include weight loss and the use of various appliances.

The tonsils, due to their size and/or position in relation to other tissues or anatomical structures of the airway, may produce vibrations and/or obstruct or restrict the airway and thusly contribute to snoring disorders and/or obstructive sleep apnea syndrome. The tonsils also may support infections and illnesses since the passageways or interstices of the tonsils can harbor bacteria. Current techniques to remove the tonsils include ablation with laser or RF energy and avulsing the tissue with standard surgical instruments such as snares, scissors or blunt dissecting instruments. Current techniques involve considerable pain and recovery time and may result in undesired blood loss. In addition, the muscular tissue level of the tonsils may be damaged resulting in increased blood loss and postoperative pain.

Electrosurgical stripping of tissue of the tonsils in layers as a treatment for snoring disorders and obstructive sleep apnea is disclosed in U.S. Pat. No. 5,423,812 to Ellman et al. Ablation of the tonsils to treat snoring disorders and/or obstructive sleep apnea syndrome is contemplated by U.S. Pat. Nos. 5,514,131, 5,624,439, 5,707,349, 5,718,702, 5,728,094, 5,730,719, 5,738,114, 5,743,904, 5,800,379, 5,807,308, 5,817,049 and 5,879,349 to Edwards, all of which disclose penetration of tissue by RF electrodes used to transmit electromagnetic energy to ablate the tissue. No teachings are provided by which ablation of the tonsils can be accomplished without penetration of the tonsils by the electrodes. U.S. Pat. Nos. 5,728,094, 5,730,719, 5,738,114, 5,800,379, 5,807,308, 5,817,049 and 5,879,349 merely allude to ultrasound as a possible source of ablative energy.

Accordingly, the need exists for methods of tonsil reduction by thermal ablation using high intensity focused ultrasound whereby one or both tonsils of a patient can be reduced, via elimination and/or alteration of the normal tissue, to thereby alleviate or eliminate vibration of the tonsil, to increase the space or size of the patient's airway and/or to treat infectious illnesses in a minimally invasive, bloodless procedure not requiring physical penetration of the tonsil by the member used to deliver the ultrasound energy and while confining ablation to a specific target area or areas within the tonsil.

SUMMARY OF THE INVENTION

Accordingly, it is a primary object of the present invention to overcome the various disadvantages of prior methods of tonsil reduction and/or removal.

It is also an object of the present invention to effect tonsil reduction by thermal ablation using high intensity focused ultrasound.

Another object of the present invention is to utilize high intensity focused ultrasound to treat airway obstructions.

A further object of the present invention is to utilize high intensity focused ultrasound to treat snoring disorders.

An additional object of the present invention is to utilize high intensity focused ultrasound to treat obstructive sleep apnea syndrome.

It is also an object of the present invention to use high intensity focused ultrasound to create a coagulative tissue area in a tonsil to permit removal of the tonsil with minimal or no blood loss.

Yet another object of the present invention is to use high intensity focused ultrasound to produce an ablated tissue area in a tonsil including unablated tissue and a plurality of lesions at which the tissue is ablated while preserving the mucosa of the tonsil.

The present invention has as a further object to use high intensity focused ultrasound to form a subsurface ablated tissue area in a tonsil including unablated tissue and relatively stiffer, ablated tissue to inhibit tonsular vibration.

The present invention also has as an object to use high intensity focused ultrasound to ablate a tonsil at an internal target area without physical penetration of the tonsil by the member used to deliver the ultrasound energy.

Still a further object of the present invention is to focus ultrasound energy within a tonsil to form an internal ablated tissue area beginning a predetermined distance beneath an external surface of the tonsil and including unablated tissue and a plurality of lesions at which the tissue is ablated.

The present invention also has as an object to focus ultrasound energy, emitted by an ultrasound emitting member, within a tonsil to ablate tissue of the tonsil at a target area beginning a predetermined distance from an active face of the ultrasound emitting member.

It is another object of the present invention to use high intensity focused ultrasound to form an ablated tissue area in a tonsil to a predetermined depth so that muscular tissue external to the tonsil capsule is not damaged.

Additionally, it is an object of the present invention to ablate a tonsil to form an ablated tissue area therein containing coagulatively necrotized tissue and being surgically removable with minimal pain and blood loss.

Some of the advantages of the present invention are that varying intensity levels of ultrasound energy can be delivered to tissue of a tonsil for varying periods of time depending on desired ablative effect, the duration of ultrasound energy delivery or application to the tissue needed to accomplish a desired ablation may be relatively brief depending on desired size for the lesions of the ablated tissue area and/or desired thermal effect on the tissue, the transducer or other member used to emit the ultrasound energy may be stationary or may be movable in order to scan a target area with focused ultrasound, a plurality of individual ablated tissue areas can be formed in a tonsil with the ablated tissue areas being separate and discontinuous or being contacting, abutting, contiguous or overlapping to form a single continuous ablated tissue area of desired size and/or shape, the ultrasound emitting member can remain stationary or can be moved along a tonsil to scan a target area with focused ultrasound, the transducer or other member may be designed with a focusing configuration designed to ensure that the lesions of the ablated tissue area have a desired cross-sectional size, begin a desired depth within the tissue and have a desired depth, a tonsil may be effectively removed or reduced in size, volume and/or configuration, tissue of a tonsil may be rigidified or stiffened via thermal damage thereto to reduce the volume of relatively softer, normal tonsular tissue, tonsil reduction and/or removal is/are accomplished with minimal trauma and pain for the patient, the transducer or other member is positioned externally adjacent or in contact with an external surface of the tonsil or is acoustically coupled with tissue of the tonsil to form an internal ablated tissue area without damaging the external tissue surface and without formation of fistulas, no external wound is presented where the mucosa of the tonsil is preserved, and an ablated tissue area of definitive size can be repeatedly and consistently produced.

These and other objects, advantages and benefits are realized with the present invention as generally characterized in a method of tonsil reduction by thermal ablation using high intensity focused ultrasound wherein an ultrasound emitting member is introduced in a patient's oral cavity and is positioned externally adjacent an external tissue surface of a tonsil. Ultrasound energy is emitted from the ultrasound emitting member into the tissue of the tonsil, and the ultrasound energy is focused within the tonsil at a plurality of focusing zones disposed beneath the external tissue surface. The focusing zones are spaced from one another and, due to focusing of the ultrasound energy at the focusing zones, the ultrasound energy is of higher or greater intensity in the tissue at the focusing zones than in the tissue surrounding the focusing zones. The tissue of the tonsil is heated at the focusing zones by the focused ultrasound energy, thereby forming an ablated tissue area containing unablated tonsular tissue and a plurality of lesions at the focusing zones, respectively, at which the tissue of the tonsil is ablated. Where the tonsil is not to be surgically removed as part of the same procedure, the ablated tissue area is preferably formed beneath the external tissue surface. Where the tonsil is to be removed surgically as part of the same procedure, the ablated tissue area may include the external tissue surface. Once an ablated tissue area of desired extent has been obtained in the tonsil, the ultrasound emitting member is withdrawn from the patient's oral cavity. The ablated tissue area may be surgically removed with minimal pain and blood loss or may be allowed to remain in the patient's body. Where the ablated tissue area is allowed to remain in the patient's body, the lesions may be subsequently degraded and absorbed by the patient's body such that the tonsil is smaller in size than prior to treatment. The lesions may subsequently remain as altered tissue, such as scar tissue that is stiffer, tighter or more rigid than the normal undamaged tonsular tissue, the volume of normal undamaged tonsular tissue therefore being less than prior to treatment. Since the tonsil is removed or is smaller in size and/or more stiff, the patient's airway is correspondingly larger in size and/or the tonsil is less likely to vibrate so as to eliminate or alleviate various airway related disorders or conditions including airway obstructions, snoring disorders and sleep apnea syndrome. In addition, the tonsil as a source of infection may be eliminated.

The ultrasound emitting member has a focusing configuration causing the ultrasound energy to be focused a predetermined distance from an active face of the ultrasound emitting member and, therefore, from the external tissue surface, so that the mucosa of the tonsil may be preserved. Also, the focusing configuration results in formation of lesions of predetermined or known depth in accordance with the length of the focusing zones, the selected ultrasound energy intensities and the selected duration times for ultrasound energy delivery. The lesion depths are selected so that the lesions do not extend deeper than desired in the tissue. The plurality of lesions may be non-contacting, with each lesion surrounded by unablated tonsular tissue. One or more of the plurality of lesions may contact another one of the plurality of lesions. The cross-sectional size of the lesions and the location and arrangement of the focusing zones in the tissue result in formation of a specific size ablated tissue area having a specific cross-sectional configuration. A single, discrete ablated tissue area or a plurality of single, discrete ablated tissue areas can be formed in the tonsil in a single procedure or treatment performed at one time or in multiple procedures or treatments performed at different times. Where a plurality of ablated tissue areas are formed, the ablated tissue areas can be contiguous, contacting, overlapping or in abutment with one another so that the ablated tissue areas together form or create a single ablated tissue area of larger cross-sectional size and/or of a desired cross-sectional configuration.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figures 1, 2, 3:
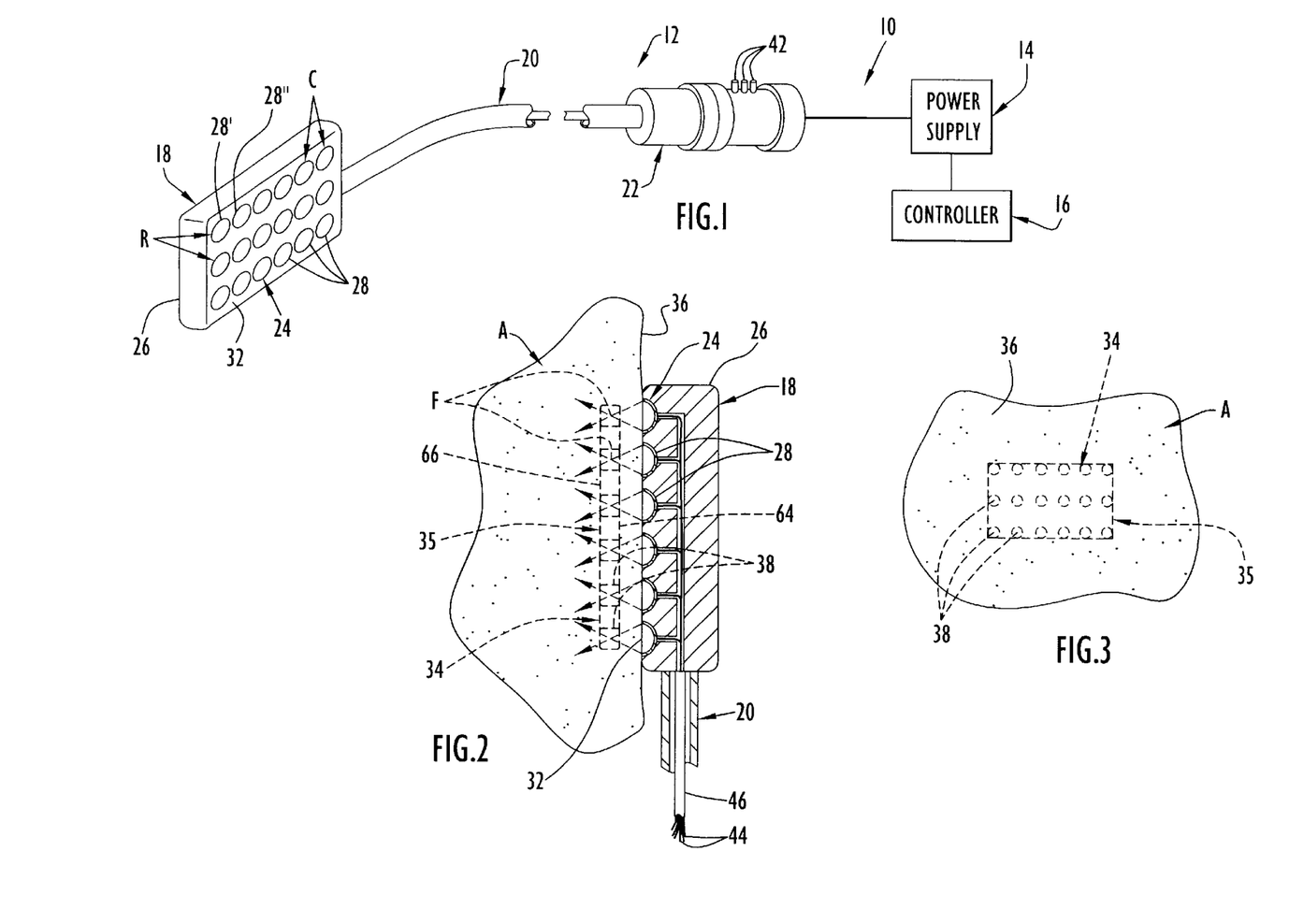
FIG. 1 is a broken perspective view, partly schematic, illustrating a high intensity focused ultrasound ablation assembly for use in the methods of the present invention.
FIG. 2 is a broken top view, partly in section, of an ultrasound emitting member of a focused ultrasound ablation device of the high intensity focused ultrasound ablation assembly and depicting focusing of ultrasound energy in anatomical tissue to form an ablated tissue area containing unablated tissue and a plurality of lesions at which the tissue is ablated.
FIG. 3 is a broken top view illustrating the surface or cross-sectional configuration of the ablated tissue area of FIG. 2.

A high intensity focused ultrasound ablation assembly or system 10 for use in the methods of the present invention is illustrated in FIG. 1 and is similar to the high intensity focused ultrasound ablation assembly described in parent U.S. patent application Ser. No. 09/487,709 and prior U.S. patent application Ser. No. 09/487,710, the disclosures of which are incorporated herein by reference. The high intensity focused ultrasound ablation assembly 10 includes a focused ultrasound ablation device 12, a power supply 14 and a controller 16. The focused ultrasound ablation device 12 is similar to that described in U.S. patent applications Ser. Nos. 09/487,709 and 09/487,710 and includes a focused ultrasound emitting member 18, an elongate handle shaft or body 20 having a distal end at which the ultrasound emitting member is disposed and a handle or handpiece 22 coupled to a proximal end of the handle shaft 20. As shown in FIGS. 1 and 2, the ultrasound emitting member includes a transducer 24 carried by or within a housing, carrier or case 26. The transducer, which includes one or more individual ultrasound emitting elements or transducer elements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical current or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration causing the ultrasound energy generated thereby to be focused, as shown by arrows in FIG. 2, at focusing zones F, respectively.

The transducer elements 28 are arranged in an array on or in housing 26; and, therefore, the transducer 24 may be considered a multi-array transducer. In the case of ultrasound emitting member 18, the transducer elements are arranged in a planar array of three rows R and six columns C, although the transducer elements can be arranged in any number of rows and columns. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different.

The transducer elements 28 can be referenced by their location in the array. For example, the transducer element 28' in the first row, first column can be designated transducer element R1C1, the transducer element 28" in the first row, second column can be designated transducer element R1C2 and so on. The transducer elements may be disposed as close as possible to one another; however, it should be appreciated that the spacing between the individual transducer elements 28 of the array can vary so that adjacent transducer elements can be disposed closer together or further apart from one another. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external side or lateral surface 32 of housing 26. The piezoelectric elements are curved in a direction inwardly of surface 32 such that ultrasound energy generated by the piezoelectric elements is emitted from focused ultrasound emitting member 18 in a direction perpendicular to surface 32 for focusing at the focusing zones F, which are spaced outwardly of surface 32. Accordingly, surface 32 is an active surface or face of the ultrasound emitting member which, when positioned externally on, adjacent or in contact with a mass, body or area of anatomical tissue A, results in the ultrasound energy emitted by the transducer being focused at zones F, which will be disposed within the anatomical tissue A as shown in FIG. 2. When the ultrasound emitting member is positioned on, against or adjacent the tissue A at a location aligned with a designated target area 34 within the tissue A, the target area being shown in dotted lines in FIGS. 2 and 3, the focusing zones will be disposed at or within the target area as best shown in FIG. 2.

Each focusing zone F consists of a single point or a plurality of points forming a zone at which the ultrasound energy is focused. Each focusing zone is in line with a central axis of the corresponding transducer element. Each focusing zone is disposed a fixed predetermined distance from a plane containing the active face 32, the predetermined distance for each focusing zone being perpendicular or normal to the active face 32. Therefore, the focusing zones F will also be disposed a predetermined perpendicular distance or a calculable or determinable perpendicular distance from an external tissue surface 36 of tissue A with which the active face 32 is placed in contact or adjacent thereto. Where the active face 32 is placed in contact with the external tissue surface 36, the perpendicular distance that zones F are disposed from external tissue surface 36 will be the same as the predetermined distance. Where the active face 32 is not placed in contact with the external tissue surface 36 but, rather, is spaced from the external tissue surface 36 by a known amount, for example, the perpendicular distance that zones F are disposed from the external tissue surface will correspond to the predetermined distance minus the distance that the active face 32 is spaced from the external tissue surface 36. Where the active face 32 is spaced from the external tissue surface 36, an acoustic coupling medium can be disposed between the external tissue surface 36 and the member 18.

Since the ultrasound is focused at focusing zones F, which are spaced from one another, the ultrasound is of greater or higher intensity at focusing zones F than in tissue surrounding the focusing zones F. Ultrasound energy is thusly focused or concentrated at the focusing zones F, causing tissue A at the focusing zones F to be heated to an ablative temperature resulting in formation of lesions 38 at the focusing zones, respectively. The tissue is ablated at the lesions 38; and, as used herein, "ablated" tissue includes tissue that has been thermally altered, damaged, necrotized, denatured, destroyed, coagulated or cauterized. When all of the transducer elements 28 are actuated, as shown in FIG. 2, heating of tissue A will occur at a focusing zone F for each transducer element, resulting in formation of a lesion 38 at each focusing zone F. The cross-sectional size of the lesions will normally depend on the width of the focusing zones. However, depending on the intensity and duration of the ultrasound energy, the lesions 38 may "grow" or "spread" somewhat beyond the focusing zones due to thermal conduction causing the dispersal or spread of heat from the focusing zones. Therefore, depending on procedural parameters and the dimensions of the focusing zones, each lesion 38 has a predetermined or predictable cross-sectional size, i.e. length and width, as well as depth. As an example, each lesion 38 spreads radially outwardly somewhat from the corresponding focusing zone. The lesions 38 have a generally circular surface or cross-sectional configuration as shown in FIG. 3 and a specific depth as shown in FIG. 2. Depending on procedural parameters, the dimensions of the focusing zones and/or the type of tissue being ablated, the lesions may or may not have a uniform cross-section along their depth. Where the focusing zones are sufficiently close together, and where the intensity of the ultrasound energy emitted from the transducer elements is sufficiently high and is applied to the tissue for a sufficient duration, the individual lesions may merge to form a single continuous lesion at the target area so that the target area is filled with ablated tissue. However, depending on the spacing between the focusing zones, and depending on the intensity of the ultrasound energy emitted from the transducer elements and the duration of ultrasound energy delivery to the tissue, the lesions 38 may remain separate, discrete and not connected to one another as shown in FIGS. 2 and 3 so that the target area contains unablated tissue and the lesions 38 at which the tissue is ablated. FIG. 3 illustrates a lesion 38 formed in tissue A for each focusing zone F wherein the lesions 38 are disposed within the target area 34 but do not merge with, contact, overlap or abut one another. Rather, each lesion 38 is surrounded or circumscribed perimetrically by unablated tissue. The non-contacting lesions 38 and unablated tissue are contained in an ablated tissue area 35 at, coincident, coextensive or aligned with the target area 34.

When all of the transducer elements 28 are actuated, an ablated tissue area of specific surface or cross-sectional configuration and size is created within the body, mass or area of anatomical tissue A for the transducer 24 in accordance with the configuration and size of the array, the intensity level of the emitted ultrasound energy, the duration or time of ultrasound energy delivery to the tissue, and the size of the lesions. Accordingly, an ablated tissue area having a specific cross-sectional length, width and depth is formed in the tissue, with the perimeter of the ablated tissue area circumscribing the array of lesions 38. FIGS. 2 and 3 illustrate, in dotted lines, the ablated tissue area 35 formed in tissue A when all of the transducer elements are actuated. The ablated tissue area 35 has a generally rectangular surface or cross-sectional configuration or area with a predetermined cross-sectional length and width shown in FIG. 3 and a predetermined cross-sectional depth, shown in FIG. 2, the cross-sectional depth corresponding to the depth of the lesions 38. When the ultrasound emitting member 18 is positioned on, against or adjacent the tissue A at a location aligned with a designated target area 34 in the tissue, the ablated tissue area 35 will be formed at or coincide with the target area as shown in FIGS. 2 and 3. The ablated tissue area is surrounded, bordered or circumscribed perimetrically by unablated tissue, as well as having unablated tissue above and below it. Since the focusing zones F begin the predetermined distance or the calculable or determinable distance below the external tissue surface 36, the ablated tissue area 35 is an internal or subsurface ablated tissue area beginning the predetermined distance or the calculable or determinable distance beneath the external tissue surface. Accordingly, the lesions 38 and ablated tissue area 35 begin at a beginning or starting margin 64 located the predetermined or calculable distance below the external tissue surface 36 and end at an ending margin 66 disposed further below the external tissue surface than the beginning margin, the distance between the beginning and ending margins corresponding to the depth of the lesions 38 and, therefore, the depth of the ablated tissue area 35.

The housing 26 can have various external configurations and sizes and can be formed by a portion of the transducer or can mount the transducer elements in various ways. The handle shaft 20 comprises an elongate, hollow or tubular member of sufficient length to position the ultrasound emitting member 18 at various operative sites in or on the body of a patient while the handle 22 is maintained at a remote location, typically externally of the patient's body. The handle shaft 20 could be solid and may comprise a bar or other shaped member. Preferably, the handle shaft 20 is malleable as disclosed in U.S. patent application Ser. No. 09/488,844, the disclosure of which is incorporated herein by reference. The handle 22 has a forward end coupled to the proximal end of handle shaft 20 and has a rearward end. The handle 22 preferably has a configuration to facilitate grasping by a surgeon or other operator. One or more controls or switches 42 may be provided on handle 22 to effect operation of the focused ultrasound ablation device.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle.

In the case of focused ultrasound ablation device 12, a transmission wire 44 is provided for each piezoelectric element and, therefore, for each transducer element. As shown in FIG. 2, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. However, the transmission wires can be disposed externally of the housing and/or the shaft. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to transducer 24 so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other non-selected transducer elements can remain deactivated to prevent transmission of electrical current thereto when the power supply is actuated or switched to an "on" mode. It should be appreciated that various components and/or methodology can be incorporated in the device 12, the power supply 14 and/or the controller 16 to permit selective actuation of selected ones of the transducer elements 28 and that such components and/or methodology would be within the purview of one skilled in the art.

Various transducers can be used in the methods of the present invention. The piezoelectric elements can be made of various piezoelectric materials such as PZT crystal materials, hard lead, zirconate/lead titanium, piezoelectric ceramic, or lithium-niobate piezoceramic material. The transducer elements can be of various sizes and can have various focusing geometries. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of anatomical tissue to be effected in response to the application or delivery of ultrasound energy to the tissue for a relatively short duration or length of time. In accordance with the present invention, the duration or length of time for ultrasound energy delivery or application to tissue of a tonsil preferably ranges from 2 to 60 seconds depending on desired lesion size and/or ablative effect.

In accordance with the methods of the present invention, high intensity focused ultrasound is used to create an ablated tissue area within tissue of a tonsil containing unablated tonsular tissue and a plurality of lesions at which the tissue of the tonsil is ablated. The ablated tissue area may be surgically removed or may be allowed to remain in the patient's body. Depending on the characteristics of the lesions of the ablated tissue area, such as the dimensions of the lesions and the nature of the thermal effect produced in the tissue of the lesions, the lesions of an ablated tissue area allowed to remain in the patient's body may be naturally degraded and absorbed by the patient's body or may remain as altered tissue, such as scar tissue that is more stiff or firm than the unablated or untreated tissue. The lesions may be entirely absorbed, may remain entirely as scar tissue, or may be partly absorbed and partly remaining as scar tissue. Where the ablated tissue area is removed surgically or where the lesions are partly or entirely absorbed, the tonsil is reduced in physical size resulting in increased airway space. In this manner, the physical size or volume of the tonsil can be reduced and/or the configuration of the tonsil can be changed in order to treat airway associated disorders or conditions including airway obstructions, snoring disorders and/or sleep apnea syndrome, and/or infectious diseases arising form the tonsil. Where the lesions remain partly or entirely as scar tissue, the scar tissue, being stiffer, firmer or more rigid than normal undamaged tissue, is more resistant to vibration or resonance thereby alleviating or eliminating snoring disorders and/or sleep apnea syndrome. In addition, the scar tissue may contract, thusly reducing the physical size of the tonsil and correspondingly increasing the size of the airway to alleviate or eliminate airway obstructions. It should be appreciated that regardless of whether the lesions are surgically removed with removal of the ablated tissue area, are naturally absorbed and eliminated or remain as scar tissue, partly or entirely, the tonsil is nonetheless "reduced". Accordingly, as used herein, "reduction" of the tonsil involves elimination or removal of normal tonsil tissue by surgical removal of an ablated tissue area, by absorption of ablated tissue and/or by transformation of normal undamaged tissue into altered tissue, such as scar tissue.

Figure 5:
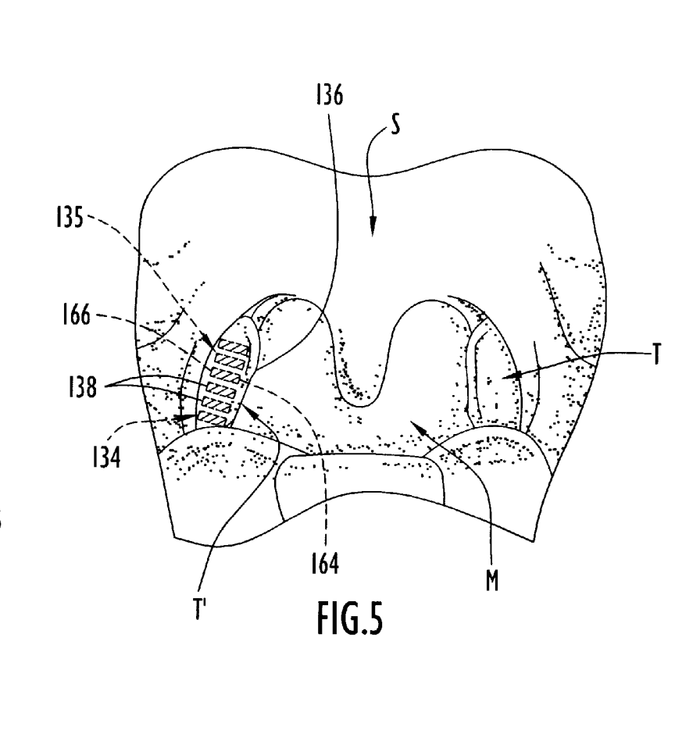
FIG. 5 is a broken anterior view illustrating the ablated tissue area of FIG. 4 formed in the right tonsil.

The tonsils T and T', as shown in FIG. 5, are glandular tissues situated on each side of the throat adjacent the tongue at the back of the mouth M and between the anterior and posterior pillars of the soft palate S. The tonsils are attached to the walls of the throat by connective tissue that forms a "capsule". Deep and exterior to the capsule is muscle. Externally, the tonsils T and T' are in relation with the inner surface of the superior constrictor muscle and comprise an external membrane or mucosa defining an external tissue surface 136. The size and thickness of the tonsils vary from person to person depending on anatomical makeup and incidences of infection. The tonsils can contribute to airway related disorders or conditions such as airway obstructions, snoring disorders and/or obstructive sleep apnea due to their thickness, size and/or disposition in relation to other anatomical tissue or structures of the airway. The passageways in the tonsils tend to harbor bacteria and thusly support infections and illness. In accordance with the present invention, high intensity focused ultrasound is used to reduce a tonsil of a patient to thereby increase the size of the patient's airway W, to rigidify the tonsil to resist vibration, to effectuate removal of the tonsil and/or to treat infectious disease.

Figure 4:
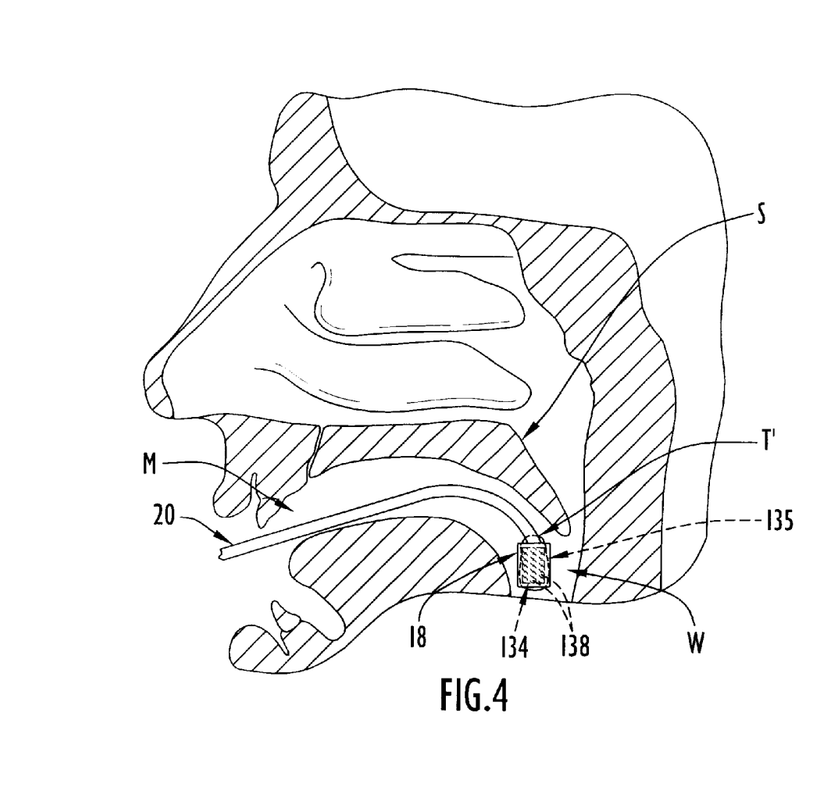
FIG. 4 is a broken side view, partly in section, illustrating use of the ultrasound emitting member of FIG. 2 to create a submucosal ablated tissue area in the right tonsil of a patient.

As shown in FIG. 4, the ultrasound emitting member 18 is introduced in the mouth or oral cavity M of a patient and is guided by the surgeon or other operator via manual manipulation of shaft 20 or its handle to position the active face 32 adjacent or in contact with the external tissue surface or mucosa 136 of the tonsil T'. The active face is placed at or on the external tissue surface 136 at a location aligned with a desired target area 134 in the tissue of the tonsil, the target area 134 being coincident, coextensive or in alignment with a desired location for formation of an ablated tissue area in the tonsil. Also, all or specific ones of the transducer elements are selected for actuation or "firing" in accordance with the desired size and configuration for the ablated tissue area and/or the desired number of lesions to be contained in the ablated tissue area. The ablation device 12 is programmed via the controller to effect actuation or "firing" of the selected transducer elements when electric current or a signal is supplied to the transducer. Of course, selection and programming for actuation or "firing" of selected transducer elements can be performed prior to introduction of member 18 in the oral cavity.

The shaft 20 is guided between the tongue and the roof of mouth M, which forms part of airway W, and the tongue can be depressed, as necessary, to facilitate introduction and positioning of the ultrasound emitting member 18 at a desired location on the tonsil. In FIGS. 4 and 5, the right tonsil T' of a patient is being treated; and, accordingly, the active face is placed against the external tissue surface of the right tonsil. Positioning of the ultrasound emitting member 18 externally adjacent or in contact with the external tissue surface 136 of the tonsil is facilitated by the configuration of shaft 20, which may correspond to the curvature of the airway W from the anterior of mouth M to the tonsil, or by the flexibility of the shaft 20 where the shaft 20 is resilient, malleable or otherwise non-rigid. Where the ultrasound emitting member is provided with the capability for imaging, guidance of the ultrasound emitting member through the airway W, proper positioning of the active face at the desired location on the tonsil and/or examination of the tonsil can be visualized from a remote location, typically externally of the patient's body. In this manner, proper placement of the active face at the desired location can be visually confirmed. Where the ultrasound emitting member is not provided with the capability for imaging, a remote viewing device such as a conventional fiber optic scope can be introduced in the airway W, typically mouth M, to provide visualization. Of course, where the location on the tonsil can be directly visualized by the surgeon, extraneous visualization aids may not be needed.

In the procedure illustrated in FIGS. 4 and 5, the active face 32 is positioned in contact with the external tissue surface 136 so that the entire array is aligned with the right tonsil T'. The location on the tonsil at which the active face is placed is coincident, coextensive or in alignment with the target area 134 within the tonsil for creation of an ablated tissue area. Once the active face is positioned in contact with the external tissue surface of the tonsil at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the tonsil at the corresponding focusing zones. In the procedure of FIGS. 4 and 5, all of the transducer elements are "fired" to emit ultrasound energy, causing the tissue of the tonsil to be heated to an ablative temperature at a focusing zone for each transducer element. The tissue at the focusing zones is heated to an ablative temperature in the range of 60 to 100 degrees Celsius and, more preferably, in the range of 60 to 90 degrees Celsius, for the time required to achieve tissue ablation. Accordingly, a plurality of subsurface, submucosal or internal ablative lesions 138 are simultaneously formed in the tonsil while the ultrasound emitting member 18 remains external of and does not physically penetrate the tonsil. Lesions 138, which are similar to lesions 38, have a generally circular surface or cross-sectional configuration as shown in FIGS. 4 and 5 but do not contact or touch one another. Lesions 138 contain ablated tonsular tissue while the tonsular tissue surrounding each lesion 138 is not heated to the ablative temperature and, therefore, is unablated. In this manner, eighteen discontinuous or non-contacting individual lesions 138 are formed in the tonsil T' as represented in FIG. 4. Lesions 138 are contained in an internal ablated tissue area 135 coincident with the target area 134, the ablated tissue area 135 containing the lesions 138 and the unablated tonsular tissue between adjacent lesions 138. The temperature to which the tissue of the lesions 138 is heated is typically sufficient to cause necrosis. The lesions 138 have a cross-sectional length, width and depth of known parameters depending on the size and focusing geometry of the transducer elements, the intensity of the ultrasound energy, the temperature to which the tissue is heated and the duration of ultrasound energy delivery or application to the tissue.

Due to the predetermined distance and the known length of the focusing zones, the lesions 138 and, therefore, the ablated tissue area 135, begin at a beginning or starting margin 164 located a predetermined or known depth beneath or below the external tissue surface 136 and end at an ending margin 166 located a greater predetermined or known depth beneath the external tissue surface 136, the distance between the beginning and ending margins corresponding to the depth of the lesions and, therefore, the depth of the ablated tissue area 135. By selecting the appropriate focusing zone depth and treatment parameters, a desired thickness or depth of unablated tissue between the beginning margin 164 and the external tissue surface 136 is disposed outside the ablated tissue area. In the method of FIGS. 4 and 5, a layer of unablated tissue about 2 mm thick is maintained between the external tissue surface 136 and the beginning or starting margin 164 of the lesions 138, thusly preserving the mucosa of the tonsil T'. The lesions 138 have a depth of about 6 mm in the direction perpendicular to tissue surface 136 such that the ablated tissue area and the lesions terminate or end at the ending margin 166 disposed a depth of about 8 mm beneath the external surface 136 at the transducer/tissue interface. By selecting the appropriate focusing zone length and treatment parameters, the depth of the ending margin 166 within the tissue is controlled thusly ensuring that the ablated tissue area and lesions do not extend to the muscular tissue exterior to the capsule of the tonsil T'.

As shown in FIG. 4, the ablated tissue area 135, which is surrounded above, below and perimetrically by unablated tissue, is similar to ablated tissue area 35 and has a surface or cross-sectional configuration or area of generally rectangular shape. The ablated tissue area 135 preferably has a cross-sectional width of about 6 mm extending along the width of the tonsil and a cross-sectional length of about 10 mm extending along the length of the tonsil, the procedure of FIGS. 4 and 5 being representative of a single treatment procedure. In the methods of the present invention, the ablated tissue areas preferably have a cross-sectional length of 2 to 20 mm, a cross-sectional width of 2 to 20 mm, and a depth of 1 to 11 mm. Where the beginning margin is disposed below the external tissue surface as in the case of ablated tissue area 135, the beginning margin is preferably disposed 1 to 4 mm below the external tissue surface. The ending margin is preferably disposed 4 to 12 mm below the external tissue surface. Although the cross-sectional length and width or other external dimensions of the ablated tissue area can be determined by the locations of the "fired" transducer elements, it should be appreciated that the cross-sectional length and/or width of the ablated tissue area can alternatively be obtained by moving the member 18 along the tonsil as described in U.S. patent application Ser. No. 09/487,709, the disclosure of which is incorporated herein by reference.

Depending on the desired lesion size and/or thermal effect, ultrasound energy will be delivered or applied to the tonsular tissue for a duration in the range of 2 to 60 seconds. The emission of ultrasound energy by ultrasound emitting member 18 is terminated by the surgeon or other operator once lesions of desired size or a desired amount of tissue ablation has been obtained, and the member 18 is withdrawn from the patient's oral cavity. In order to terminate the emission of ultrasound energy by the ultrasound emitting member, the power supply is deactivated or switched to an "off" mode so that electrical current is no longer supplied to the selected piezoelectric elements. FIG. 5 illustrates the oral cavity subsequent to withdrawal of member 18 therefrom. Confirmation of lesion size and/or ablated tissue area size can be obtained via ultrasound imaging of the tonsil.

The lesions 138, which typically contain necrotized tissue, may be naturally degraded and absorbed, partially or entirely, by the patient's body such that the right tonsil T' will be smaller in physical bulk, size or volume than it was prior to treatment. Accordingly, the patient's airway W will be larger in size than it was prior to treatment thusly eliminating or alleviating airway related conditions or disorders such as airway obstructions, snoring disorders and sleep apnea syndrome. The lesions 138 may remain, partly or entirely, as relatively stiffer or firmer scar tissue such that a lesser amount of relatively softer, normal tonsular tissue remains, whereby the tonsil is of increased resistance to vibration or resonance thusly eliminating or alleviating snoring disorders and sleep apnea syndrome. Also, the ablated tonsil is less likely to harbor bacteria and other germs. The left tonsil T of the patient can be reduced as part of the same procedure or as part of a different procedure performed at a later time. Reduction of the left tonsil T may not be necessary where reduction of the right tonsil T' is sufficient to treat the particular condition.

Figure 6:
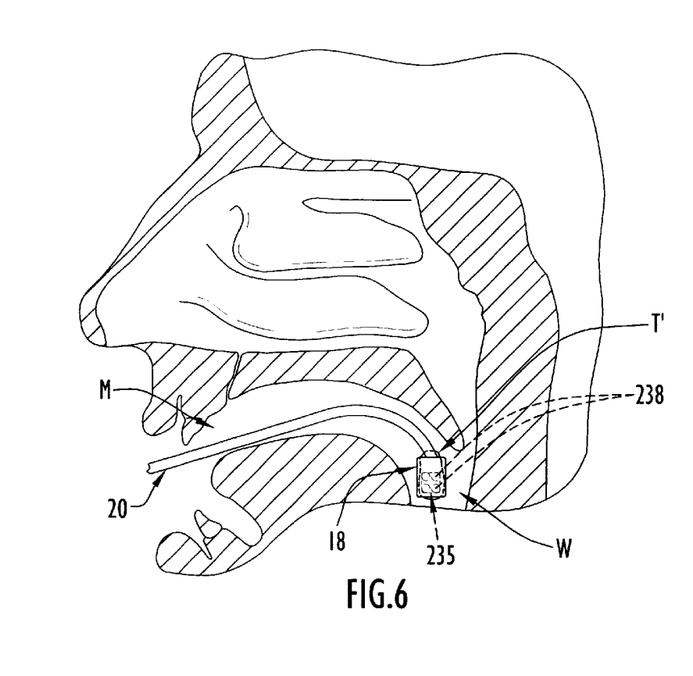
FIG. 6 is a broken side view, partly in section, illustrating use of the ultrasound emitting member of FIG. 2 to form an alternative ablated tissue area in the right tonsil.
Figure 7:
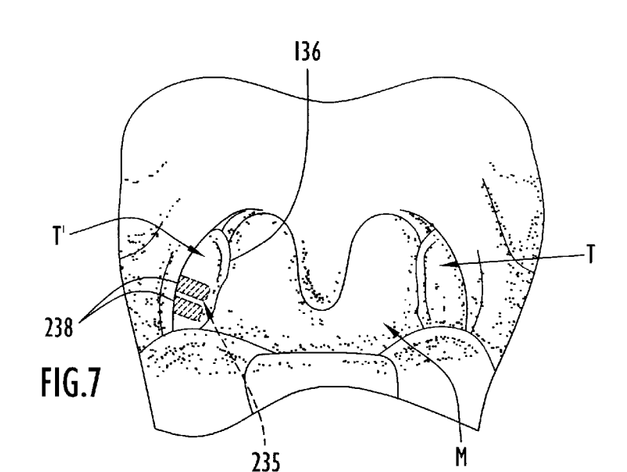
FIG. 7 is a broken anterior view illustrating the alternative ablated tissue area of FIG. 6 formed in the right tonsil.

FIGS. 6 and 7 illustrate formation of an alternative ablated tissue area 235 in the right tonsil T' of a patient in accordance with the present invention. The ultrasound emitting member 18 is used to form ablated tissue area 235 at a desired target area in the bottom or lower end portion of the right tonsil T'. The ablated tissue area 235 is similar to ablated tissue area 135 except that it is of generally square surface or cross-sectional configuration and contains four generally circular lesions 238 each surrounded by unablated tissue. The ablated tissue area 235 can be formed using the ultrasound emitting member 18 by selecting and "firing" transducer elements R1C1, R1C2, R2C1 and R2C2, for example, to emit ultrasound energy. As described for the procedure illustrated in FIGS. 4 and 5, the ultrasound energy emitted by the selectively "fired" or actuated transducer elements is focused in the tonsil T' at a focusing zone for each actuated transducer element, causing subsurface lesions 238 to be formed in the right tonsil at the focusing zones corresponding to transducer elements R1C1, R1C2, R2C1 and R2C2. The lesions 238 are similar to lesions 138 but are larger in diametric size than lesions 138. The ablated tissue area 235 is surrounded by unablated tissue above, below and perimetrically.

Figure 8:
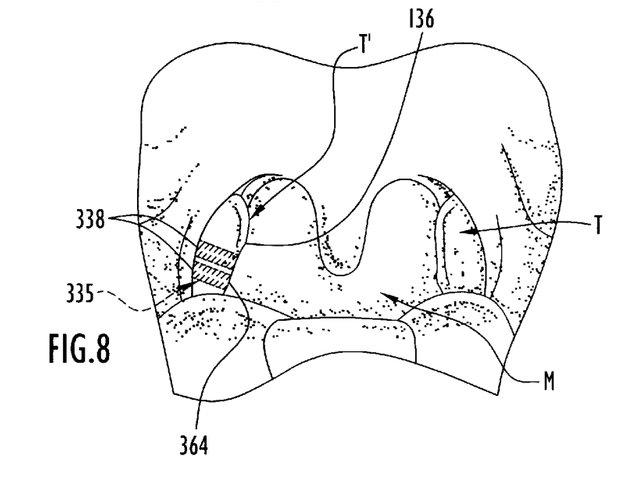
FIG. 8 is a broken anterior view illustrating a further alternative ablated tissue area formed in the right tonsil.
Figure 9:
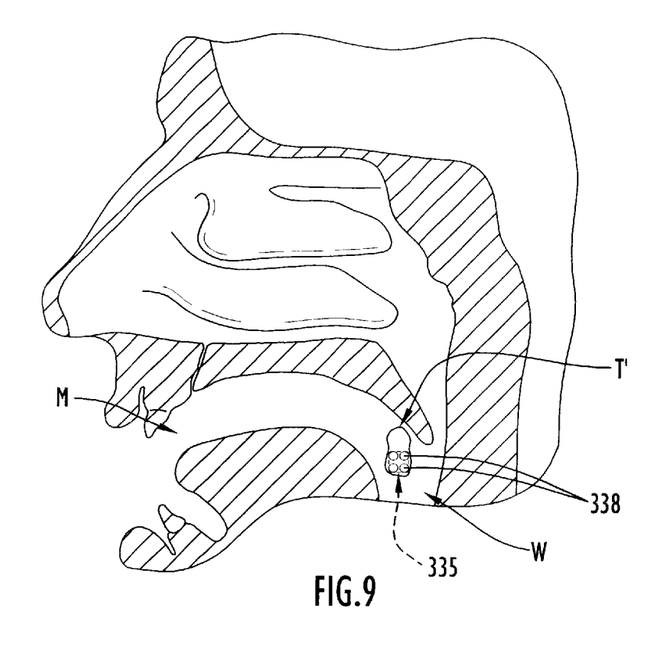
FIG. 9 is a broken side view, partly in section, illustrating the further alternative ablated tissue area of FIG. 8 formed in the right tonsil.

FIGS. 8 and 9 illustrate another alternative ablated tissue area 335 formed in the right tonsil T' of a patient. Ablated tissue area 335 is similar to ablated tissue area 235 except that the four non-contacting lesions 338 of ablated tissue area 335 include the mucosa or external tissue surface 136 but not the muscular tissue level or capsule of the right tonsil T'. Accordingly, the starting margin 364 for ablated tissue area 335 and lesions 338 is coincident with external tissue surface 136. In a preferred method, the ablated tissue area 335 has a cross-sectional length of about 12 mm extending along the length of the tonsil, a cross-sectional width of about 12 mm extending along the width of the tonsil and a depth of about 5 mm, which corresponds to the depth of the lesions 338. The tonsil T' is thereby ablated down to but not beyond the level of its capsule so as to preserve the muscular tissue level. Subsequent to creation of ablated tissue area 335, the ablated tissue area 335 is surgically removed or incised with minimal or no blood loss and minimal pain due to the majority of the tissue thereof having been coagulatively necrotized. The ablated tissue area 335 may be removed as part of the ablation procedure. The ablated tissue area 335 can be removed, without the muscular tissue, using a suitable instrument or instruments that does/do not introduce additional damaging energy to the remaining tonsular tissue in order to minimize post-operative pain.

Figure 10:
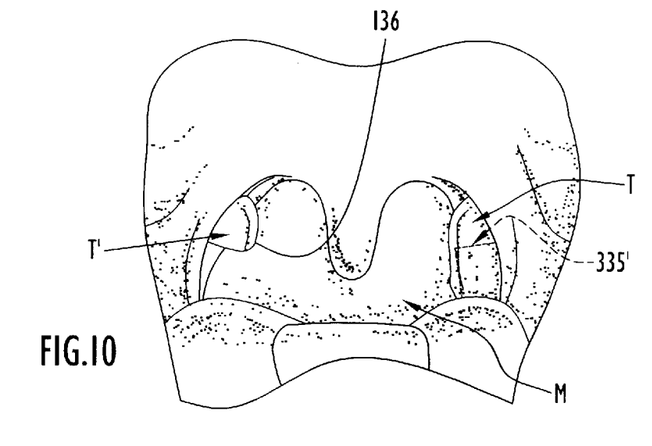
FIG. 10 is a broken anterior view depicting the right tonsil following removal of the further alternative ablated tissue area.

Since the muscular tissue is not damaged by heat or instruments, increased blood loss and post-operative pain are avoided. FIG. 10 illustrates the right tonsil T' subsequent to surgical removal of ablated tissue area 335 so that only an upper or top portion of the right tonsil T' remains. With the lower portion of the right tonsil thusly removed, the airway W is of increased size, and the impact of the right tonsil as a source of illness or disease is reduced or eliminated. An ablated tissue area similar to ablated tissue area 335 can be formed in the left tonsil T of the patient and can be removed subsequent to its formation as described for ablated tissue area 335. The ablated tissue area can be formed in and removed from the left tonsil T as part of the same procedure performed for formation and removal of the ablated tissue area of the right tonsil T' or in a separate procedure performed at a different time. FIG. 10 illustrates in dotted lines an ablated tissue area 335' formed in the left tonsil T of the patient.

Figure 11:
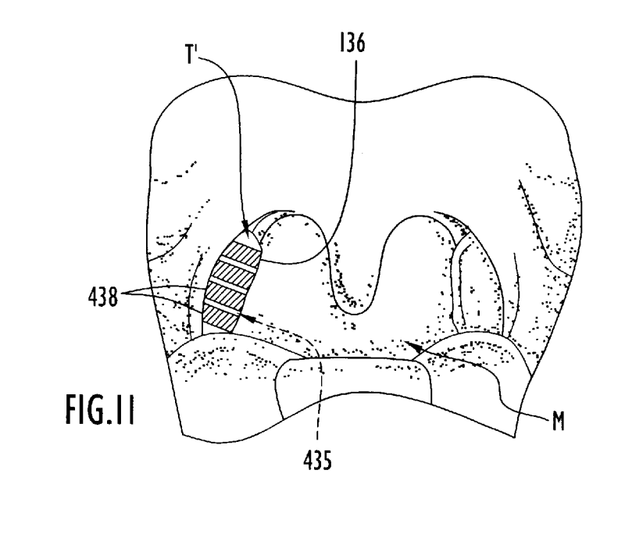
FIG. 11 is a broken anterior view illustrating another alternative ablated tissue area formed in the right tonsil of a patient.

FIG. 11 illustrates a further alternative ablated tissue area 435 formed in the right tonsil T' of a patient in accordance with the present invention. The ablated tissue area 435 is similar to ablated tissue area 335 except that the ablated tissue area 435 encompasses both the bottom or lower portion and the top or upper portion of the tonsil T'. Accordingly, ablated tissue area 435 contains unablated tonsular tissue and eight non-contacting lesions 438, at which the tonsular tissue is ablated. The ultrasound emitting member 18 can be used to form ablated tissue area 435 by activating the appropriate transducer elements. The lesions 438 and, therefore, the ablated tissue area 435 include the mucosa or external tissue surface 136 but not the muscular tissue level exterior to the tonsil capsule. The tonsil is thereby ablated down to but not beyond the level of its capsule so as to preserve the muscular tissue level. Subsequent to creation of ablated tissue area 435, the ablated tissue area 435 is surgically removed or incised as described above with minimal or no blood loss due to the majority of the tissue thereof having been coagulatively necrotized.

Figure 12:
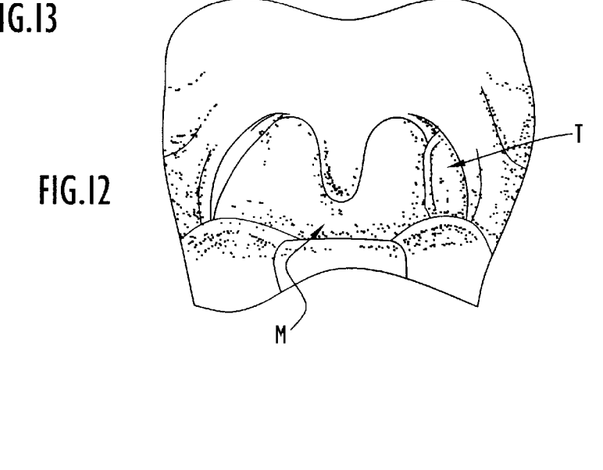
FIG. 12 is a broken anterior view illustrating the patient's oral cavity following removal of the another alternative ablated tissue area of FIG. 11 to effect removal of the right tonsil.

Since the muscular tissue is not damaged by heat or instruments, increased blood loss and post-operative pain are avoided. FIG. 12 illustrates the oral cavity or mouth M subsequent to removal of ablated tissue area 435 whereby the entire right tonsil T', but not the muscular tissue, has been removed. Accordingly, removal of one or both tonsils of a patient can be accomplished to treat diseases of the tonsil/tonsils and/or infections arising therefrom and/or to treat airway related disorders by increasing the size of the airway W due to removal of all or part of the tonsil/tonsils. An ablated tissue area similar to ablated tissue area 435 can be formed in the left tonsil T of the patient and can be removed subsequent to its formation as described for ablated tissue area 435. The ablated tissue area can be formed in and removed from the left tonsil as part of the same procedure performed for formation and removal of the ablated tissue area of the right tonsil or in a separate procedure performed at a different time.

Figure 13:
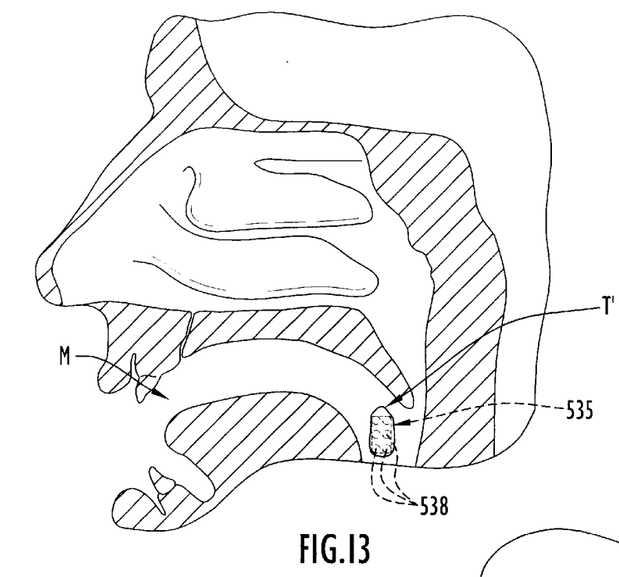
FIG. 13 is a broken side view, partly in section, illustrating an additional alternative ablated tissue area formed in the right tonsil of a patient.

FIG. 13 illustrates an alternative ablated tissue area 535 formed in the right tonsil T' and containing six generally circular, subsurface or submucosal lesions 538 each surrounded by unablated tissue. The ablated tissue area 535 can be formed in the right tonsil using ultrasound emitting member 18 by activating six appropriate transducer elements as described above.

Figure 14:
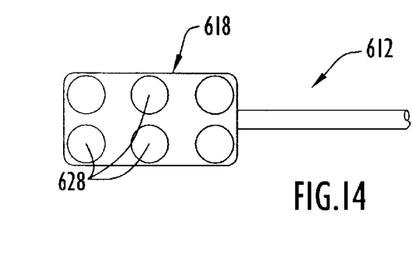
FIG. 14 is a broken side view of an alternative focused ultrasound ablation device having a modified ultrasound emitting member for use in the methods of the present invention.

It should be appreciated that the methods of tonsil reduction according to the present invention can be performed using focused ultrasound ablation devices wherein the transducer elements of the ultrasound emitting members are not selectively actuatable. For example, FIG. 14 illustrates an alternative focused ultrasound ablation device 612 having focused ultrasound emitting member 618, which is similar to focused ultrasound emitting member 18 except that focused ultrasound emitting member 618 includes an array of six transducer elements 628 actuatable simultaneously or in unison to emit ultrasound energy. The transducer elements 628 are arranged in two rows and three columns and are used to form an ablated tissue area containing six lesions, such as ablated tissue area 535. Accordingly, it should be appreciated that various dedicated ultrasound emitting members having different arrays and/or numbers of transducer elements can be provided, with a particular ultrasound emitting member being capable of obtaining a particular ablated tissue area of predetermined size, configuration and number of lesions in response to actuation of all of the transducer elements of the particular ultrasound emitting member.

Figure 15:
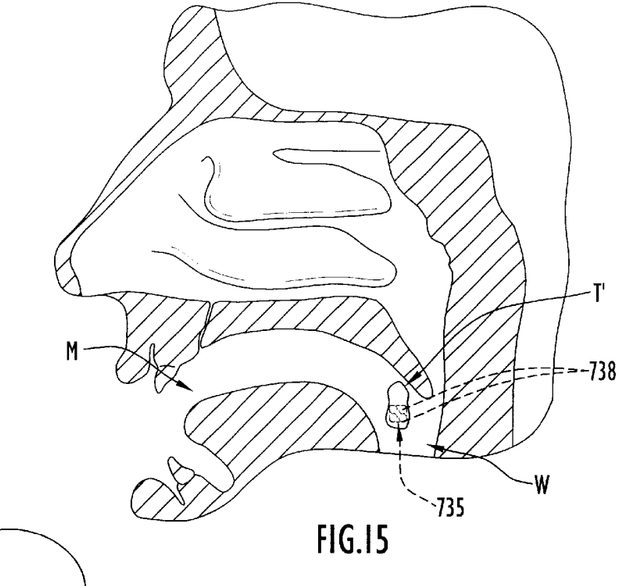
FIG. 15 is a broken side view, partly in section, illustrating yet another alternative ablated tissue area formed in the right tonsil of a patient.

FIG. 15 illustrates an alternative, subsurface ablated tissue area 735 formed in the right tonsil T' in a manner similar to ablated tissue area 235. However, the ultrasound energy used to form ablated tissue area 735 is of higher intensity and/or is applied to the tissue of the tonsil for a longer duration than the energy used to form ablated tissue area 235. Accordingly, the lesions 738 of ablated tissue area 735 have a generally circular surface or cross-sectional configuration larger in diameter that the generally circular cross-sectional configuration of lesions 238 due to greater dispersal of heat from the focusing zones. As a result, the lesions 738 contact or touch one another but do not merge sufficiently to fill the entire ablated tissue area 735 with ablated tissue. Although each lesion 738 is not completely surrounded perimetrically by unablated tissue, there is still some unablated tissue within the ablated tissue area 735 as shown by unablated tissue disposed between adjacent lesions 738. It should be appreciated, therefore, that the ablated tissue areas formed in accordance with the present invention can include a plurality of non-contacting lesions each completely surrounded by unablated tissue and/or a plurality of contacting lesions with unablated tissue between the contacting lesions.

In the procedures described and illustrated above, the ultrasound emitting member is placed against a tonsil at a desired location to form an ablated tissue area of final size and configuration in the tonsil with focused ultrasound energy generated and emitted by the ultrasound emitting member without moving the member from the desired location. It should be appreciated, however, that where the largest size ablated tissue area capable of being formed in a tonsil with the ultrasound emitting member is smaller than the final size and/or different from the final configuration desired for the ablated tissue area, the ultrasound emitting member can be moved along the tonsil to form an ablated tissue area of desired final size and configuration as explained in U.S. patent application Ser. No. 09/487,709.

The methods of the present invention allow tonsil reduction or removal to be performed with minimal trauma and pain for the patient and with faster healing and recovery times. The mucosa or other external tissue surface can be preserved so that no external wound is presented or exposed. A single ablation treatment in accordance with the present invention may be sufficient to eliminate various airway related disorders and/or tonsular diseases or infections since an ablated tissue area of sufficient size may be obtained in one or both tonsils of a patient with a single treatment. By controlling the delivery of ultrasound energy to the tissue, the temperature to which the tissue is heated by the ultrasound energy can be controlled to avoid undesired patient responses. The ultrasound emitting members can be provided with sensors for monitoring the amount of ultrasound energy delivered to the tissue and/or for detecting the temperature to which the tissue is heated, which can be provided as feedback to the controller. The delivery of ultrasound energy to the tissue can be controlled to achieve a selected temperature in the tissue, a selected amount of ablation, a desired lesion size or a desired duration of ultrasonic energy delivery. The ultrasound emitting members can be disposable or can be designed to be reusable and thusly can be capable of being sterilized to medical standards. The ultrasound emitting members can be provided with disposable covers or guards which can be removed and discarded after use so that the ultrasound emitting members can be reused. The transducer or transducer elements can be removable from the ultrasound emitting members allowing disposability of the ultrasound emitting members and reuse of the transducer or transducer elements in another ultrasound emitting member. The ultrasound emitting members can be introduced at internal operative sites through catheters or sleeves with the ultrasound emitting members disposed within the catheters or sleeves during introduction and being extended from the catheters or sleeves following introduction at the operative sites. The ultrasound emitting members can be immobilized during use as may be accomplished with various types of stabilizing members provided on the shafts or on the ultrasound emitting members. The focused ultrasound ablation devices can be provided with imaging capabilities or can be used with various imaging devices as disclosed in U.S. patent application Ser. No. 09/487,709. The focused ultrasound ablation devices can be provided with cooling systems for cooling the ultrasound emitting members and/or the transducers as disclosed in U.S. patent application Ser. No. 09/487,709. The methods of tonsil reduction can be performed using an acoustic coupling medium as disclosed in U.S. patent application Ser. No. 09/487,709. A single ultrasound emitting member can be used to form various different ablated tissue areas of various sizes, configurations, and number of lesions depending on the particular transducer elements selected for actuation. A plurality of different ultrasound emitting members having non-selectively actuatable transducer elements can be provided with each ultrasound emitting member having a different array and/or number of transducer elements to obtain a particular ablated tissue area of predetermined size, configuration and number of lesions when all of the transducer elements of the ultrasound emitting members are actuated. Any number of ablated tissue areas can be formed in a tonsil with each ablated tissue area surrounded by unablated tissue or with the ablated tissue areas contiguous to, in abutment with, contacting or overlapping one another to form a single ablated tissue area. The ultrasound emitting members, the transducers and/or the transducer elements can be moved relative to the tissue to scan target areas with focused ultrasound energy, and such scanning can be accomplished in various diverse ways. The ablated tissue areas can include unablated tissue and a plurality of non-contacting lesions, a plurality of contacting lesions or a combination of contacting and non-contacting lesions.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of thermal ablation of a tonsil comprising the steps of introducing an ultrasound emitting member in a patient's oral cavity;

positioning the ultrasound emitting member adjacent an external tissue surface of one of the patient's tonsils;

emitting ultrasound energy from the ultrasound emitting member into the tissue of the one tonsil;

focusing the ultrasound energy at a plurality of focusing zones contained in a target area in the one tonsil;

heating the tissue of the one tonsil at the focusing zones with the focused ultrasound energy to form an ablated tissue area at the target area containing unablated tissue of the one tonsil and a plurality of lesions at the focusing zones, respectively, at which the tissue of the one tonsil is ablated;

withdrawing the ultrasound emitting member from the oral cavity; and allowing the lesions to be absorbed by the patient's body so that the one tonsil is reduced in physical size.

2. The method of thermal ablation of a tonsil as recited in claim 1 wherein said step of focusing includes focusing the ultrasound energy in a target area disposed beneath the external tissue surface.

3. The method of thermal ablation of a tonsil as recited in claim 2 wherein said step of heating includes heating the tissue of the one tonsil at the focusing zones with the focused ultrasound energy to achieve a temperature in the range of 60 to 100 degrees Celsius.

4. The method of thermal ablation of a tonsil as recited in claim 3 wherein said step of heating includes heating the tissue of the one tonsil at the focusing zones with the focused ultrasound energy so that the lesions begin at a beginning margin located below the external tissue surface of the one tonsil.

5. The method of thermal ablation of a tonsil as recited in claim 4 wherein said step of heating includes heating the tissue of the one tonsil at the focusing zones with the focused ultrasound energy so that the lesions begin at a beginning margin located 1 to 4 mm below the external tissue surface of the one tonsil.

6. The method of thermal ablation of a tonsil as recited in claim 5 wherein said step of heating includes heating the tissue of the one tonsil at the focusing zones with the focused ultrasound energy so that the lesions end at an ending margin located 4 to 12 mm below the external tissue surface of the one tonsil.

7. The method of thermal ablation of a tonsil as recited in claim 6 wherein said step of heating includes heating the tissue of the one tonsil at the focusing zones with the focused ultrasound energy for a duration in the range of 2 to 60 seconds.

8. The method of thermal ablation of a tonsil as recited in claim 1 wherein said step of heating includes forming the ablated tissue area surrounded by unablated tissue of the one tonsil.

9. A method of thermal ablation of a tonsil comprising the steps of
introducing an ultrasound emitting member in a patient's oral cavity;
positioning the ultrasound emitting member adjacent an external tissue surface of one of the patient's tonsils;
emitting ultrasound energy from the ultrasound emitting member into the tissue of the one tonsil;
focusing the ultrasound energy at a plurality of focusing zones contained in a target area in the one tonsil;
heating the tissue of the one tonsil at the focusing zones with the focused ultrasound energy to form an ablated tissue area at the target area containing unablated tissue of the one tonsil and a plurality of lesions at the focusing zones, respectively, at which the tissue of the one tonsil is ablated, said step of heating including forming the ablated tissue area surrounded by unablated tissue of the one tonsil, said step of heating including forming the ablated tissue area so that the plurality of lesions do not contact one another; and
withdrawing the ultrasound emitting member from the oral cavity.

10. The method of thermal ablation of a tonsil as recited in claim 8 wherein said step of heating includes forming the ablated tissue area so that at least one of the plurality of lesions contacts another of the plurality of lesions.

11. A method of thermal ablation of a tonsil comprising the steps of
introducing an ultrasound emitting member in a patient's oral cavity;
positioning the ultrasound emitting member adjacent an external tissue surface of one of the patient's tonsils;
emitting ultrasound energy from a plurality of ultrasound emitting elements of the ultrasound emitting member;
focusing the ultrasound energy in the one tonsil at a plurality of spaced focusing zones corresponding to the ultrasound emitting elements, respectively;
ablating the tissue of the one tonsil with the focused ultrasound energy to form an ablated tissue area containing unablated tissue of the one tonsil and a plurality of lesions at the focusing zones, respectively, at which the tissue of the one tonsil is ablated;
withdrawing the ultrasound emitting member from the oral cavity; and
allowing the lesions to be replaced with scar tissue so that the one tonsil is rendered more resistant to vibration.

12. The method of thermal ablation of a tonsil as recited in claim 11 wherein said step of ablating includes forming the plurality of lesions to begin at a beginning margin located below the external tissue surface of the one tonsil, to end at an ending margin located further below the external tissue surface of the one tonsil than the beginning margin and to have a depth between the beginning and ending margins in the range of 1.0 to 11.0 mm.

13. The method of thermal ablation of a tonsil as recited in claim 12 wherein said step of ablating includes forming the plurality of lesions to begin at a beginning margin located about 2 mm below the external tissue surface of the one tonsil.

14. The method of thermal ablation of a tonsil as recited in claim 13 wherein said step of ablating includes forming the plurality of lesions to end at an ending margin located about 8 mm below the external tissue surface of the one tonsil.

15. The method of thermal ablation of a tonsil as recited in claim 11 wherein said step of ablating includes forming the ablated tissue area with a cross-sectional length in the range of 2 to 20 mm.

16. The method of thermal ablation of a tonsil as recited in claim 15 wherein said step of ablating includes forming the ablated tissue area with a cross-sectional width of 2 to 20 mm.

17. A method of tonsil reduction comprising the steps of
introducing an ultrasound emitting member in a patient's oral cavity;
positioning the ultrasound emitting member adjacent an external tissue surface of one of the patient's tonsils;
emitting ultrasound energy from a plurality of ultrasound emitting elements of the ultrasound emitting member;
focusing the ultrasound energy in the one tonsil at a plurality of spaced focusing zones corresponding to the ultrasound emitting elements, respectively;
ablating the tissue of the one tonsil with the focused ultrasound energy to form an ablated tissue area containing unablated tissue of the one tonsil and a plurality of lesions at the focusing zones, respectively, at which the tissue of the one tonsil is ablated, said step of ablating including forming the plurality of lesions to begin at a beginning margin coincident with the external tissue surface of the one tonsil and to end at an ending margin located below the external tissue surface of the one tonsil;
withdrawing the ultrasound emitting member from the oral cavity; and
surgically removing the ablated tissue area.

18. A method of thermal ablation of a tonsil comprising the steps of introducing an ultrasound emitting member in a patient's oral cavity;

positioning the ultrasound emitting member adjacent the mucosa of one of the tonsils of the patient;

actuating selected ones of a plurality of ultrasound emitting elements of the ultrasound emitting member to emit ultrasound energy;

emitting ultrasound energy from the selected ultrasound emitting elements into the one tonsil;

focusing the ultrasound energy in the one tonsil at a plurality of spaced focusing zones corresponding to the selected ultrasound emitting elements, respectively;

ablating the tissue of the one tonsil with the focused ultrasound energy to form an ablated tissue area containing unablated tissue of the one tonsil and a plurality of lesions at the focusing zones, respectively, at which the tissue of the one tonsil is ablated;

withdrawing the ultrasound emitting member from the oral cavity; and allowing the lesions to be replaced with scar tissue so that the stiffness of the one tonsil is increased.

19. A method of thermal ablation of a tonsil comprising the steps of introducing an ultrasound emitting member in a patient's oral cavity;

positioning the ultrasound emitting member adjacent the mucosa of one of the tonsils of the patient;

actuating selected ones of a plurality of ultrasound emitting elements of the ultrasound emitting member to emit ultrasound energy;

emitting ultrasound energy from the selected ultrasound emitting elements into the one tonsil;

focusing the ultrasound energy in the one tonsil at a plurality of spaced focusing zones corresponding to the selected ultrasound emitting elements, respectively;

ablating the tissue of the one tonsil with the focused ultrasound energy to form an ablated tissue area containing unablated tissue of the one tonsil and a plurality of lesions at the focusing zones, respectively, at which the tissue of the one tonsil is ablated, said step of ablating including forming the ablated tissue area in substantially the entire one tonsil;

withdrawing the ultrasound emitting member from the oral cavity; and surgically removing the ablated tissue area to thereby remove the entire one tonsil without the capsule thereof.

20. The method of thermal ablation of a tonsil as recited in claim 18 and further including, prior to said step of actuating, the step of selecting the ultrasound emitting elements to be actuated.

21. The method of thermal ablation of a tonsil as recited in claim 18 wherein said step of focusing includes focusing the ultrasound energy at a plurality of focusing zones disposed below the mucosa.

22. The method of thermal ablation of a tonsil as recited in claim 18 wherein said step of ablating includes forming the plurality of lesions beneath the mucosa.

23. A method of thermal ablation of a tonsil comprising the steps of introducing an ultrasound emitting member in a patient's oral cavity;

positioning the ultrasound emitting member adjacent an external tissue surface of one of the patient's tonsils;

emitting ultrasound energy from the ultrasound emitting member into the tissue of the one tonsil;

focusing the ultrasound energy at a plurality of focusing zones contained in a target area in the one tonsil;

heating the tissue of the one tonsil at the focusing zones with the focused ultrasound energy to form an ablated tissue area at the target area containing unablated tissue of the one tonsil and a plurality of lesions at the focusing zones, respectively, at which the tissue of the one tonsil is ablated;

withdrawing the ultrasound emitting member from the oral cavity; and allowing the ablated tissue area to remain in the patient's body so that the one tonsil is rendered more resistant to germs.

* * * * *